(12) United States Patent
Shimizu et al.

(10) Patent No.: US 8,496,819 B2
(45) Date of Patent: Jul. 30, 2013

(54) SEPARATION COLUMN FOR LIQUID CHROMATOGRAPH APPARATUS AND LIQUID CHROMATOGRAPH APPARATUS USING THEREOF

(75) Inventors: Katsutoshi Shimizu, Hitachinaka (JP);
 Masahito Ito, Hitachinaka (JP);
 Kimihiko Ishii, Hitachinaka (JP);
 Yoshihiro Nagaoka, Ishioka (JP);
 Kisaburo Deguchi, Sapporo (JP);
 Takefumi Yokokura, Kasama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 644 days.

(21) Appl. No.: 12/146,912

(22) Filed: Jun. 26, 2008

(65) Prior Publication Data

US 2009/0001007 A1 Jan. 1, 2009

(30) Foreign Application Priority Data

Jun. 28, 2007 (JP) ................. 2007-169887
Apr. 21, 2008 (JP) ................. 2008-110471

(51) Int. Cl.
 *B01D 15/08* (2006.01)
 *G01N 30/02* (2006.01)
 *C02F 1/28* (2006.01)
(52) U.S. Cl.
 USPC ......... 210/198.2; 210/656; 422/70; 73/61.52; 435/803
(58) Field of Classification Search
 USPC ............................................ 210/198.2, 656
 See application file for complete search history.

(56) References Cited

U.S. PATENT DOCUMENTS 6,863,820 B2 * 3/2005 Cabrera et al. ................ 210/635
2004/0120871 A1 * 6/2004 De Angelis et al. .......... 422/222
2005/0155933 A1 * 7/2005 Ma ................................ 210/656

FOREIGN PATENT DOCUMENTS

| JP | 11-064314 | 3/1999 |
| JP | 2002-505005 | 2/2002 |
| JP | 2002-536651 | 10/2002 |
| WO | WO 98/59238 | 12/1998 |
| WO | WO 00/47304 | 8/2000 |
| WO | WO 2007/021037 | 2/2007 |

OTHER PUBLICATIONS

Japanese Office Action issued in Japanese Patent Application No. 2008-110471 dated May 29, 2012.

* cited by examiner

*Primary Examiner* — Katherine Zalasky

(74) *Attorney, Agent, or Firm* — McDermott Will & Emery LLP

(57) ABSTRACT

Both a column having high-pressure resistance and capable of performing high-speed separation and analysis even with a small flow rate and a liquid chromatograph apparatus using the column are provided. A separation column according to the present invention has a monolithic rod being arranged in the center, being made of a porous material, and having a circular cross section, a filler layer arranged such that it encircles a circumferential surface of the monolithic rod, and a cylindrical support medium arranged outside the filler layer. The filler layer is formed by filling a tube-like gap between the monolithic rod and the support medium with particles or beads.

9 Claims, 2 Drawing Sheets

SEPARATION COLUMN FOR LIQUID CHROMATOGRAPH APPARATUS AND LIQUID CHROMATOGRAPH APPARATUS USING THEREOF

BACKGROUND OF THE INVENTION

1. Field of the Invention

The present invention relates to a separation column for separating components in a liquid sample and a liquid chromatograph apparatus using thereof.

2. Description of the Related Art

In a high speed liquid chromatograph apparatus, a particle-filling column has been used as a column for separating components in a liquid sample. In recent years, however, a monolithic-type column is increasingly used, instead of the particle-filling column. A monolithic-type silica column, for example, is known as a monolithic-type column.

A monolithic-type silica column includes a narrow tube and a porous body inserted therein. The porous body is called a monolithic rod, a monolithic silica rod or the like. The porous body is a thin rod body. Therefore, it is very difficult to form a porous body with high precision such that the outside diameter of a cross section thereof is constant along the length direction. Thus, a gap is generally generated between a narrow tube and a porous body.

When passing through a porous body, a liquid leaks into the gap through an outer circumferential surface thereof. The liquid leaked into the gap flows inside the gap without going back into the porous body.

Japanese Patent Application Laid-Open No. 11-64314 proposes to provide a resin cladding material on the outer circumferential surface of a porous body to prevent leakage of a liquid from the outer circumferential surface of the porous body into a surrounding gap.

A resin cladding material to be attached to the outer circumferential surface of a porous body needs to have strong adhesive properties to porous bodies and also high-pressure resistance. It is difficult to find a material satisfying such conditions.

When passing through a porous body, a liquid comes into contact with a resin cladding material on the outer circumferential surface thereof. Thus, a volatile solvent in the resin cladding material is eluted, degrading separation performance.

An object of the present invention is to provide both a column having high-pressure resistance and capable of performing high-speed separation and analysis even with a small flow rate and a liquid chromatograph apparatus using the column.

SUMMARY OF THE INVENTION

A separation column according to the present invention has a monolithic rod being arranged in the center, being made of a porous material, and having a circular cross section, a filler layer arranged such that it encircles a circumferential surface of the monolithic rod, and a cylindrical support medium arranged outside the filler layer. The filler layer is formed by filling a tube-like gap between the monolithic rod and the support medium with particles or beads.

According to the present invention, both a column having high-pressure resistance and capable of performing high-speed separation and analysis even with a small flow rate and a liquid chromatograph apparatus using the column can be provided.

EXPLANATIONS OF LETTERS OF NUMERALS

Figure 1:
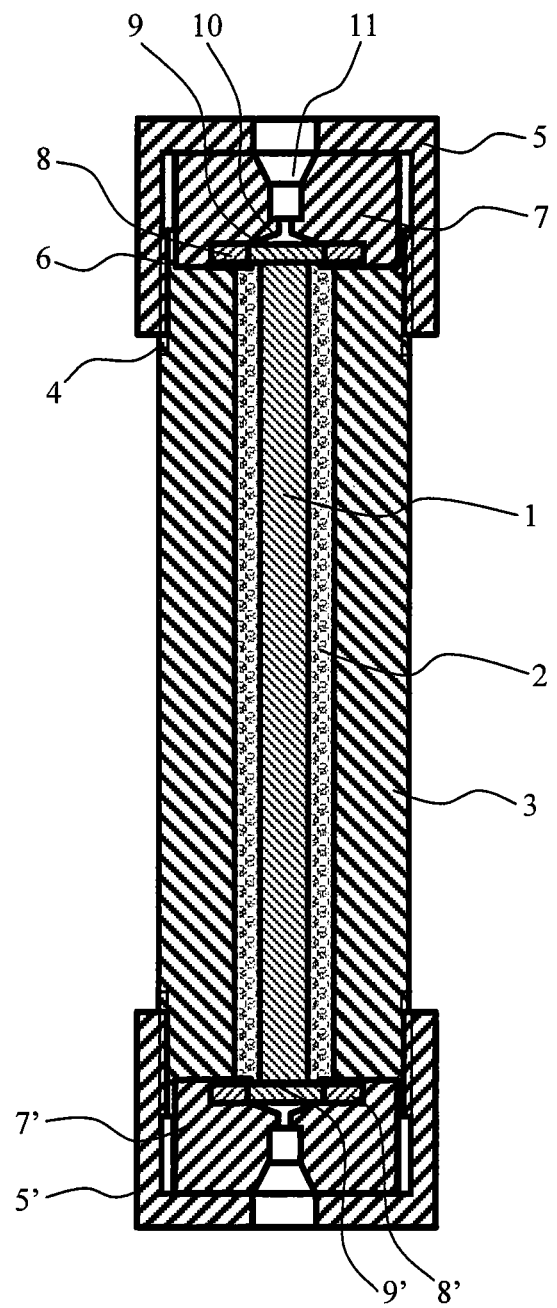
FIG. 1 is a drawing exemplifying a configuration of a separation column for a liquid chromatograph apparatus according to the present invention.

1: Monolithic rod
2: Filler layer
3: Support medium
4: Screw
5, 5': Fixing member
6: Screw
7, 7': Connection member
8, 8': Sealant
9, 9': Filter
10: Inflow port
11: Connection part
201: Eluting solution vessel
203: Liquid feeding pump
204: Auto-sampler
202: Sample vessel
205: Column oven
205a: Separation column
206: Detector
207: Waste liquid vessel

DESCRIPTION OF THE PREFERRED EMBODIMENTS

The configuration of a separation column according to the present invention will be described with reference to FIG. 1. The separation column in the present embodiment has a separation column part in the center, an upstream connection part on an upstream side thereof, and a downstream connection part on a downstream side thereof. The separation column part has a monolithic rod 1 being arranged in the center and having a circular cross section, a tube-like filler layer 2 outside thereof, and a cylindrical support medium 3 on the outermost side. The monolithic rod 1, the filler layer 2, and the support medium 3 are concentrically arranged and have the same length in the axial direction. The filler layer 2 is formed by filling a tube-like gap between the support medium 3 and the monolithic rod 1 with particles or beads.

The upstream connection part has a circular filter 9, a ring-shaped sealant 8, a columnar connection member 7, and a cup-shaped fixing member 5. The filter 9 and the sealant 8 are arranged on the monolithic rod 1 and the connection member 7 is arranged thereon. The fixing member 5 and the connection member 7 have a through hole extending along the central axis line. The through hole of the connection member 7 is tapered on the external surface side and the internal surface side of the connection member. A connection part 11 is formed by the hole of the fixing member 5 and the hole portion of the connection member 7 on the external surface side. An inflow port 10 is formed by the hole portion of the connection member 7 on the internal surface side. The diameter of an opening of the inflow port 10 is slightly smaller than the inside diameter of the support medium 3. The outside diameter of the filter 9 is substantially equal to the diameter of the opening of the inflow port 10. That is, the outside diameter of the filter 9 is larger than that of the monolithic rod 1 and smaller than the inside diameter of the support medium 3. The sealant 8 is used to prevent a liquid from leaking from the outer circumference of the filter 9 and is arranged on the outer circumference of the filter 9.

A screw 6 formed on the inner surface of the fixing member 5 and a screw 4 formed on the outer circumference of the support medium 3 are configured to engage with each other. By tightening the screw 6 of the fixing member to the screw 4 of the support medium, the connection member 7, the filter 9, and packing 8 are closely fixed to ends of the separation column by the fixing member 5. The downstream connection part has a configuration similar to that of the upstream connection part.

Next, materials of a separation column according to the present invention will be described. The monolithic rod 1 is a member in a columnar or rod shape, which is made of a porous material formed by molding silica, glass, quartz or a compound thereof. Unevenness of several to several tens of micrometers is formed on the outer circumferential surface of the monolithic rod 1.

The filler layer 2 is formed from particles or beads. Particles or beads are formed from silica, silica having octadecyl groups chemically bound to itself, stainless steel, TEFLON® polytetrafluoroethylene (PTFE), DIFLON® polychlorotrifluoroethylene, zirconia, ceramic, PEEK (polyether ether ketone), VESPEL® poly-N,N'-(p,p'-oxydiphenylene pyromellitimide, sapphire, ruby, diamond, alumina, glass, quartz, titanium, or UHMW (ultrahigh molecular weight) polyethylene. The diameter of such particles is 1 to 2 μm. Particles may be spherical and crushed beads may also be used.

Particles or beads constituting the filler layer 2 are preferably formed from the same material as that of the monolithic rod 1. The monolithic rod 1 is formed from silica, glass, quartz, or the like, based on silicon dioxide. Therefore, it is desirable that the filler layer 2 be similarly formed from silica, glass, quartz, or the like.

The support medium 3, the connection member 7, and the fixing member 5 may be constituted by stainless, but also by materials other than stainless. The material of the filter 9 is obtained, for example, by hardening powder of SUS (stainless used steel). Since the filter 9 has infinitesimal gaps inside, foreign matter whose diameter is larger than that of such infinitesimal gaps can be eliminated.

The assembly method of a separation column according to the present invention will be described. First, the monolithic rod 1 is inserted into the support medium 3. A tube-like gap is thereby formed between the monolithic rod 1 and the support medium 3. Next, the gap is filled with particles or beads. A packer is used to fill the gap with particles or beads while gradually increasing the flow rate. The filler layer 2 is thereby formed. Unevenness of several to several tens of micrometers has been formed on the outer circumferential surface of the monolithic rod 1. The diameter of such particles or beads is 1 to 2 μm. Therefore, the gap between the monolithic rod 1 and the support medium 3 can be densely filled with particles or beads. The monolithic rod 1 and the filler layer 2 are closely in contact and due to friction between the monolithic rod 1 and the filler layer 2, the monolithic rod 1 will not be shifted in the axial direction, relative to the filler layer 2. After the separation column part being formed in this manner, an upstream connection part and a downstream connection part are attached thereto.

Functions of the separation column according to the present invention will be described. An inflow pipe (not shown) is connected to the connection part 11 of the connection member 7 to feed a liquid containing a sample to be separated. The liquid is led to the inflow port 10 and passed through the filter 9 before being flown into the monolithic rod 1. The liquid flows toward the outflow side (downward direction in FIG. 1) inside the monolithic rod 1 while repeating desorption. Accordingly, chemical components constituting the sample are separated on a component by component basis before being detected by a detector arranged at an outlet of the separation column.

Pressure of the liquid inside the monolithic rod 1 and the filler layer 2 decreases along the length direction, that is, along the axial direction, but remains constant along the radial direction. Pressure of the liquid is maintained not only by the monolithic rod 1, but also by the filler layer. Therefore, pressure to be shared by the monolithic rod 1 is reduced.

When the liquid is flown toward the separation column with high pressure, the monolithic rod 1 is prevented from being moved relatively in the axial direction with respect to the filler layer 2 by friction generated between the monolithic rod 1 and the filler layer 2. Therefore, pressure-resistant performance of the separation column is improved.

Performance of a separation column according to the present invention will be calculated below. It is generally known that a pressure drop in the separation column can be calculated from the formula of Kozeny-Carman shown as Formula 1.

$$\Delta P = uL\eta/K \quad \text{(Formula 1)}$$

$\Delta P$ is a pressure difference between an inlet and an outlet of the separation column, u is the linear flow rate, $\eta$ is the viscosity of a liquid, L is the length of a column (the monolithic rod 1), and K is the permeability. The pressure drop $\Delta P$ represents flow resistance. Therefore, as is clear from Formula 1, the flow resistance is inversely proportional to the permeability K. That is, the flow resistance decreases with the increasing permeability K.

The permeability K depends on the surface area of a solid phase in contact with a liquid. According to a study by the inventors of the present application, the permeability K of the monolithic rod 1 is $4 \times 10^{-14}$ m$^2$. The permeability K of a filler layer made of beads whose particle diameter is 1 to 2 μm is $1.8 \times 10^{-15}$ m$^2$ to $7 \times 10^{-15}$ m$^2$. Therefore, the permeability K of the monolithic rod 1 is about 6 to 20 times that of the filler layer 2.

The diameter of the monolithic rod 1 is determined by Formula 2 shown below.

$$u = F/[\pi(D/2)^2 \epsilon] \quad \text{(Formula 2)}$$

u is the linear velocity, F is the flow rate, D is the diameter of the monolithic rod 1, and $\epsilon$ is the porosity of the monolithic rod 1. The porosity of the monolithic rod 1 is about 0.6 to 0.8. The linear velocity u is assumed to be constant (10 mm/s). The flow rate is set ½ to twice that of a general liquid chromatograph apparatus. The flow rate of the general liquid chromatograph apparatus is 1.0 mL/min. Therefore, the flow rate is set to 0.5 to 2.0 mL/min in the present embodiment. Substituting these values into Formula 2 yields the outside diameter of the monolithic rod 1 ranging from 1.2 to 2.8 mm. Therefore, the outside diameter of the monolithic rod 1 is made desirably 2 mm or less, allowing for making the outside diameter smaller.

While a conventional separation column uses a monolithic rod whose diameter is about 4 mm, a separation column in the present invention can use a monolithic rod whose diameter is 2 mm or less. Thus, the amount of liquid being fed can be reduced to ¼.

In addition, from a practical standpoint, an easy-to-use column that can be used in a flow rate region of 1.0 ml/min or less widely used by a general high-speed liquid chromatograph apparatus can be provided.

In order to shorten the analysis time, the linear velocity can be increased. That is, high pressure is applied. The maximum pressure of a high-pressure liquid chromatograph apparatus is, for example, 5 to 60 MPa.

When a liquid is flown into the separation column, it is preferable that the liquid selectively flow through the monolithic rod 1. That is, the flow rate of liquid flowing through the monolithic rod 1 is desirably sufficiently larger than that of liquid flowing through the filler layer 2. The ratio of the flow rate of liquid flowing through the monolithic rod 1 to that of liquid flowing through the filler layer 2 depends not only on the ratio of a sectional area of the monolithic rod 1 to that of the filler layer 2, but also on the ratio of the permeability K of the monolithic rod 1 to that of the filler layer 2. It is assumed that the outside diameter of the monolithic rod 1 is 1.2 to 2.8 mm and the thickness of the filler layer 2 in the radial direction is 0.01 to 0.5 mm. It is also assumed that the permeability K of the monolithic rod 1 is $4 \times 10^{-14}$ m$^2$ and that of the filler layer is $1.8 \times 10^{-15}$ m$^2$ to $7 \times 10^{-15}$ m$^2$. Pressure of a liquid fed to the separation column is assumed to be 5 to 60 MPa. According to a tentative calculation by the inventors of the present application, the flow rate of liquid flowing through the monolithic rod 1 is about 100 to 1000 times that of liquid flowing through the filler layer 2. Therefore, in the present embodiment, when a liquid is flown into the separation column, the liquid selectively flows through the monolithic rod 1.

Moreover, when a liquid is flown into the separation column, the monolithic rod 1 may be clogged due to a physical or chemical factor. In such a case, the liquid flows through the filler layer 2. Therefore, the separation column itself will not be blocked by clogging. By adopting the same material for the filler layer 2 as that of the monolithic rod 1, misplaced materials can be prevented from being eluted from the filler layer 2.

The length in the flow direction, that is, the length of the separation column part is calculated from Formula 3 shown below.

$$H = L/N \quad \text{(Formula 3)}$$

H is the theoretical plate height, L is the length of the separation column part, and N is the number of theoretical plates. As performance of a general separation column, the theoretical plate height H is assumed to be 10 μm and the number N of theoretical plates to be 10000. In this case, the length L of the separation column part will be 100 mm. However, the length L of the separation column part depends on the sample to be separated and the analysis time. Thus, in the present invention, it is desirable to set the length L of the separation column part to 30 to 200 mm.

According to the present invention, as described above, the filler layer 2 is formed by filling a gap between the support medium 3 and the monolithic rod 1 with particles or beads. Thus, a separation column whose pressure-resistance performance is improved and which is capable of separating and analyzing a sample at high speed with a small flow rate can be realized.

Figure 2:
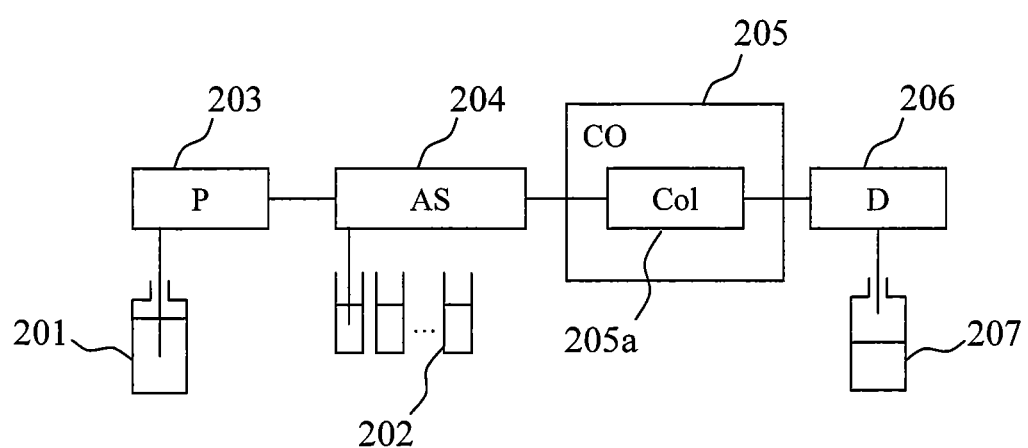
FIG. 2 exemplifies an outline configuration of a liquid chromatograph apparatus to which the separation column in the present invention is applied.

The configuration of a liquid chromatograph apparatus according to the present invention will be exemplified with reference to FIG. 2. The liquid chromatograph apparatus has an eluting solution vessel 201, a liquid feeding pump 203, an auto-sampler 204, a column oven 205, a separation column 205a, a detector 206, and a waste liquid vessel 207. An eluting solution contained in the eluting solution vessel 201 is sucked by the liquid feeding pump 203 and fed to the auto-sampler 204. In the auto-sampler 204, a sample from a sample vessel 202 is injected into the eluting solution via an injection port.

The sample and eluting solution are mixed before being sent to the separation column 205a arranged inside the column oven 205. In the separation column 205a, the sample is separated on a component by component basis before being sent to the detector 206.

In the detector 206, components contained in the sample are analyzed. The detector 206 is comprised of a light source (not shown), flow cells, an optical sensor and the like. A waste liquid containing the sample whose analysis by the detector 206 is completed is recovered by the waste liquid vessel 207.

The separation column shown in FIG. 1 is used in a liquid chromatograph apparatus in the present invention. Thus, the amount of consumed eluting solution will not increase even if the analysis time is shortened by increasing the velocity of flow of a liquid.

An embodiment of the present invention has been described, but the present invention is not limited to the above embodiment and it is easily understood by those skilled in the art that the present invention can be variously modified within the scope of the present invention defined by claims.

What is claimed is:

1. A separation column for a liquid chromatograph apparatus having a monolithic rod being arranged in a center and made of a porous body and having an uneven outer surface, a filler layer arranged such that it encircles the monolithic rod, a cylindrical support medium arranged outside the filler layer, a filter positioned on the end of the monolithic rod, and a sealant arranged on the outer circumference of the filter, wherein:

the filler layer is formed by densely filling a tube-like space between the monolithic rod and the support medium with particles or beads, the particles or beads have a diameter that is 1 to 2 μm and is smaller than the unevenness on the outer surface of the monolithic rod, the monolithic rod has an outside diameter of 1.2 to 2.8 mm, and the diameter of the filter is larger than the outer diameter of the monolithic rod and smaller than the inner diameter of the support medium.

2. The separation column according to claim 1, wherein the monolithic rod and the filler layer are formed from an identical material.

3. The separation column according to claim 1, wherein the monolithic rod and the filler layer are formed from a material made of at least one of silica, glass, and quartz.

4. The separation column according to claim 1, wherein the filler layer is formed from particles or beads formed from silica, silica having octadecyl groups chemically bound to itself, stainless, polytetrafluoroethylene (PTFE), polychlorotrifluoroethylene, zirconia, ceramic, PEEK (polyether ether ketone), poly-N,N'-(p,p'-oxydiphenylene pyromellitimide, sapphire, ruby, diamond, alumina, glass, quartz, titanium, or UHMW (ultrahigh molecular weight) polyethylene.

5. The separation column according to claim 1, wherein the filler layer is formed from spherical particles or crushed beads.

6. The separation column according to claim 1, wherein the monolithic rod has a length of 30 to 200 mm.

7. The separation column according to claim 1, wherein the monolithic rod has an outside diameter of 1.2 to 2.8 mm and the filler layer has a thickness of 0.01 to 0.5 mm in a radial direction.

8. A liquid chromatograph apparatus comprising the separation column according to claim 1.

9. A liquid chromatograph apparatus comprising the separation column according to claim 5.

* * * * *